United States Patent [19]

Troxler, Sr. et al.

[11] Patent Number: 4,979,197
[45] Date of Patent: Dec. 18, 1990

[54] NUCLEAR RADIATION APPARATUS AND METHOD FOR DYNAMICALLY MEASURING DENSITY OF TEST MATERIALS DURING COMPACTION

[75] Inventors: William F. Troxler, Sr.; Ali Regimand, both of Raleigh, N.C.

[73] Assignee: Troxler Electronic Laboratories, Inc., Research Triangle Park, N.C.

[21] Appl. No.: 312,128

[22] Filed: Feb. 17, 1989

Related U.S. Application Data

[63] Continuation-in-part of Ser. No. 865,776, May 22, 1986, abandoned.

[51] Int. Cl.$^5$ ............................................. G01B 15/02
[52] U.S. Cl. ...................................... 378/90; 378/86; 378/308
[58] Field of Search ............................ 378/86, 88, 89; 250/253, 308

[56] References Cited

U.S. PATENT DOCUMENTS

| | | |
|---|---|---|
| 2,781,453 | 2/1957 | Belcher et al. |
| 3,341,706 | 9/1967 | Swift et al. ............................ 250/253 |
| 3,354,310 | 11/1967 | Swift ...................................... 250/253 |
| 3,426,206 | 2/1969 | Lehman et al. |
| 3,628,375 | 12/1971 | Pagar . |
| 4,208,581 | 6/1980 | Kaneko . |
| 4,417,466 | 11/1983 | Panetti . |
| 4,422,322 | 12/1983 | Spangler . |
| 4,439,675 | 3/1984 | Campbell . |
| 4,467,212 | 8/1984 | Olcott . |
| 4,473,319 | 9/1984 | Spangler . |
| 4,525,854 | 6/1985 | Molbert et al. |
| 4,641,030 | 2/1987 | Regimand . |
| 4,651,556 | 3/1987 | Seaman . |

FOREIGN PATENT DOCUMENTS 0108845 5/1984 European Pat. Off.

OTHER PUBLICATIONS

"New Methods for Cost Saving Pavement Evaluation", Better Roads, Jul. 1983, pp. 24–25.
Trade literature from "Seaman Nuclear Corporation", Oak Creek, Wis., Model DOR-1000 Density Measuring System, 8 pages.

Primary Examiner—Carolyn E. Fields
Assistant Examiner—David P. Porta
Attorney, Agent, or Firm—Bell, Seltzer, Park & Gibson

[57] ABSTRACT

The present invention provides an apparatus and method for dynamically measuring the density of soil, asphaltic material and the like during the compaction of the material. The gauge includes a nuclear radiation source and a nuclear radiation detector means which are mounted in spaced relation from the surface of the test material to form an air gap therebetween. The gauge also includes means for measuring the size of the air gap between the test material and the source and detector system, and means to compensate for the effect of the size of the air gap to thereby obtain the density of the test material.

10 Claims, 3 Drawing Sheets fig. 4.

NUCLEAR RADIATION APPARATUS AND METHOD FOR DYNAMICALLY MEASURING DENSITY OF TEST MATERIALS DURING COMPACTION

CROSS-REFERENCE TO RELATED APPLICATIONS

This is a continuation-in-part of commonly owned copending application Ser. No. 865,776, filed May 22, 1986, now abandoned.

FIELD AND BACKGROUND OF THE INVENTION

The present invention relates to an apparatus and method for determining the density of test materials, and more particularly to a nuclear radiation measurement apparatus and method for measuring the density of soil, asphaltic materials and the like during movement of the radiation measurement apparatus across the surface of the material which is undergoing measurement.

Nuclear radiation gauges for determining the density of soil and asphaltic materials are well-known, as described for example in U.S. Pat. No. 2,781,453. Such gauges employ the phenomenon of scattering of gamma rays and are known by those skilled in the art as "scatter" gauges.

Such gauges typically take the form of a hand held portable instrument which is positioned on the surface of the test material for a predetermined period of time while backscattered radiation is counted to obtain a density reading. Devices of this type have been widely used and well accepted in the industry for obtaining rapid non-destructive density measurements of the test material. The density gauges are particularly useful in determining the degree of compaction of soil or asphalt during the construction of roadbeds and pavement surfaces, in which heavy rollers or compactors are rolled back and forth across the surface and density readings are made periodically using the portable stationary nuclear density gauges of the type described above.

It has been recognized that it would be quite desirable to obtain a readout of density continuously during the compaction operation, rather than periodic spot density readings. This approach would give a density reading over a large area rather than an instantaneous spot reading, and would also make it possible to more rapidly respond to changes in the density readouts during the compaction operation. To this end, several movable, dynamically reading nuclear density gauges have been proposed. One such gauge is in the form of a wheeled unit and employs a pair of small cylindrical rolls as wheels with a nuclear source and detector mounted between the rolls in a suspended, noncontacting relationship with the underlying test surface. The gauge rides along the pavement surface and may be connected to and pulled by a pavement compactor vehicle. Another such gauge, described in published European Patent Application No. 108,845, has the nuclear radiation source and detector mounted inside a cylindrical roll, and the roll may be manually pushed along the pavement surface or propelled therealong by connecting it to a pavement compactor vehicle.

Both of these gauges assume a constant spacing (air gap) between the source/detector system and the underlying pavement surface. However, the density reading obtained from a backscatter gauge through an air gap is quite sensitive to variations in the size of the gap. During operation, any buildup of asphalt on the rolls will increase the effective diameter of the rolls and alter the size of the air gap between the source/detector system and the surface of the underlying test material, introducing error in the density reading.

Mobile nuclear density gauges are also disclosed in U.S. Pat. Nos. 3,341,706 and 3,354,310. These patents disclose a mobile nuclear gauge which can be towed by a vehicle along a roadway or surface to obtain a continuous logging of the density and moisture. The gauge is mounted in a trailer above the road surface. The patents recognize that in order to obtain an accurate measurement, the air gap between the gauge and the surface must be maintained as nearly constant as possible, and they attempt to accomplish this by providing soft tires on the trailer vehicle so that roughness is absorbed by the soft tires. The '706 patent mentions that as an alternative to maintaining a constant air gap, it may be desirable to monitor the air gap by suitable optic, mechanical, nuclear or sonic means and to compensate for the differences which may occur in the air gap. However, the patent gives no indication of how this compensation might be accomplished.

It is an object of the present invention to provide a nuclear density measurement method and apparatus for dynamically measuring pavement density and which overcomes the above-noted disadvantages and limitations of the prior art.

It is a further object of the present invention to provide a nuclear density measurement method and apparatus which is particularly suited to be used by a pavement compactor vehicle during a pavement compaction operation.

SUMMARY OF THE INVENTION

In accordance with the present invention an apparatus and method is provided in which the nuclear source/detector system is mounted for movement in spaced relation above the surface of the test material and wherein the spacing between the nuclear source/detector system and the underlying test surface is monitored as the nuclear density reading is being taken, and any variations in the spacing are taken into account and corrected for during the measurement.

In accordance with the invention, a method is provided for measuring the density of a test material using a nuclear radiation backscatter gauge including a nuclear radiation source and nuclear radiation detector means positioned in spaced relation to the source, and wherein the method comprises the steps of: moving the source and detector along the test material while maintaining the source and detector in spaced relation above the surface of the test material to form an air gap therebetween, obtaining a count of the photons which are backscattered to the detector by the test material, obtaining a measurement which represents the size of the air gap between the surface of the test material and the source/detector means, and calculating the density of the test material as a function of the count of backscattered photons and said measurement of the air gap.

The method and apparatus of the present invention are especially suited for use during the compaction of soil or pavement material using a compactor vehicle to obtain a real-time readout of pavement density so that the operator of the compactor vehicle can determine when the optimum amount of compaction has been achieved. To this end, the gauge is provided with a computer means for performing real-time calculations, and the method of the present invention comprises:

moving the source and detector relative to the test material while maintaining the source and detector in spaced relation above the surface of the test material to form an air gap therebetween, obtaining a count of the photons which are backscattered to the detector means by the test material storing said count as a value in a predetermined memory location in said computer means, obtaining a measurement which represents the size of the air gap between the surface of the test material and the detector means and storing said air gap measurement as a value in said computer means, and storing in said computer means, values defining an empirically derived relationship between the air gap measurement and the calibration constants A, B and C for the density equation $$D = \frac{1}{B} \ln\left(\frac{A}{CR + C}\right)$$

calculating with said computer means, values for the calibration constants A, B and c for said density equation using said stored values defining said empirically derived relationship and using said stored value for the air gap measurement; and calculating with said computer means, the density of the test material, using the thus calculated calibration constants A, B and C and the stored photon count in the density equation $$D = \frac{1}{B} \ln\left(\frac{A}{CR + C}\right)$$

In accordance with a further aspect of the present invention there is provided a nuclear radiation gauge which is mounted on a compactor vehicle for providing the operator of the vehicle with a readout of the density or degree of compaction during operation of the vehicle. The compactor vehicle has rollers for compaction of materials such as soil, asphalt pavement and the like and a vehicle chassis connected to the rollers. In combination with this there is provided a nuclear density gauge means for measuring the density of the material during operation of the compactor vehicle. The gauge means comprising a nuclear radiation source, nuclear radiation detector means mounted in a predetermined spaced relation from the source, and means for suspendingly mounting said source and said detector means from said vehicle chassis with the source and detector means being located in spaced relation from the surface of the material undergoing compaction so that the source is positioned for emitting nuclear radiation through the air space beneath the gauge means and into the material and the detector means is positioned for detecting backscattered radiation from the material, means cooperating with said detector means for obtaining a count of the photons which are backscattered to the detector means by the test material, means for measuring the size of the air gap between the surface of the test material and the detector means, and means for calculating the density of the test material as a function of said count of backscattered photons and said measurement of the air gap.

BRIEF DESCRIPTION OF THE DRAWINGS

Some of the features and advantages of the invention having been stated, others will become apparent from the detailed description which follows and from the accompanying drawings, in which.

DESCRIPTION OF THE ILLUSTRATED EMBODIMENT

Referring now more specifically to the drawings, the reference character 10 generally indicates a compactor vehicle of the type which is conventionally used for rolling and compacting soils, paving materials and the like. The compactor vehicle includes a chassis 11 and large diameter smooth surfaced rollers 12, 13, mounted to the chassis 11 and serving as the wheels of the compactor vehicle. As illustrated, a driver's seat 14 is located in the central portion of the vehicle chassis, and suitable controls 15 are provided to enable the driver to control the direction and speed of the vehicle. As is conventional, suitable motor means (not shown) is provided for propelling the vehicle along the pavement.

The nuclear density measurement apparatus of the present invention comprises two units, a sensor unit 20 mounted beneath the compactor vehicle and located close to the surface of the pavement, and a console unit 40 accessible to the driver's seat 14 at the top of the vehicle. The sensor unit 20 and the console unit 40 are interconnected by a cable 21. The console unit 40 includes a keyboard 41 by which the operator may control the operation of the gauge and a display 42 by which the density reading obtained by the gauge as well as other information, is communicated to the operator. The mounting of the components of the sensor apparatus in this manner makes it possible to measure the pavement density during the operation of the compactor vehicle, and to rapidly provide the operator of the vehicle with a readout of pavement density. This makes it possible for the vehicle operator to immediately know when he has completed a sufficient number of rolling passes to achieve a desired degree of compaction. In the preferred embodiment illustrated in the drawings, the console unit is equipped with a pair of signal lights, such as a green light 44 and a red light 45. The operator can enter into the console unit via the keyboard 41, a setpoint representing the desired target density to be achieved in the material by operation of the compactor vehicle. As the compactor unit is being operated, the density which is calculated by the system is continually compared to the setpoint value. As long as the actual density is less than the setpoint, the green light 44 is illuminated, indicating to the operator that continued rolling and compaction is required. When the actual density equals or exceeds the setpoint density, then the red light 45 is illuminated, giving the operator an immediate visual indication that the desired density has been achieved, and that he can now move the compactor to another area.

Figure 1:
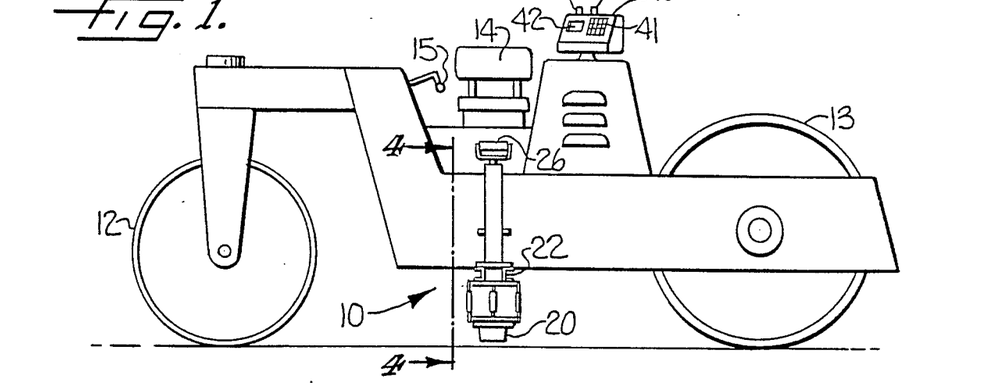
FIG. 1 is a side elevational view of a compactor vehicle upon which is mounted a nuclear density gauge in accordance with the present invention.
Figure 2:
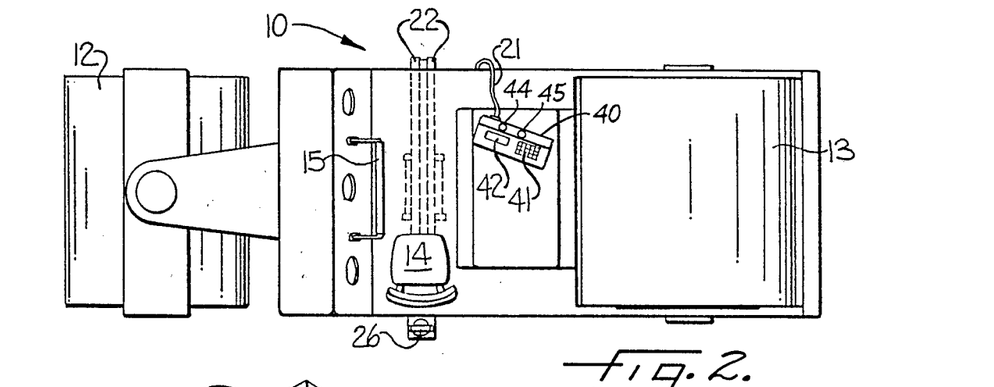
FIG. 2 is a top elevational view thereof.
Figure 3:
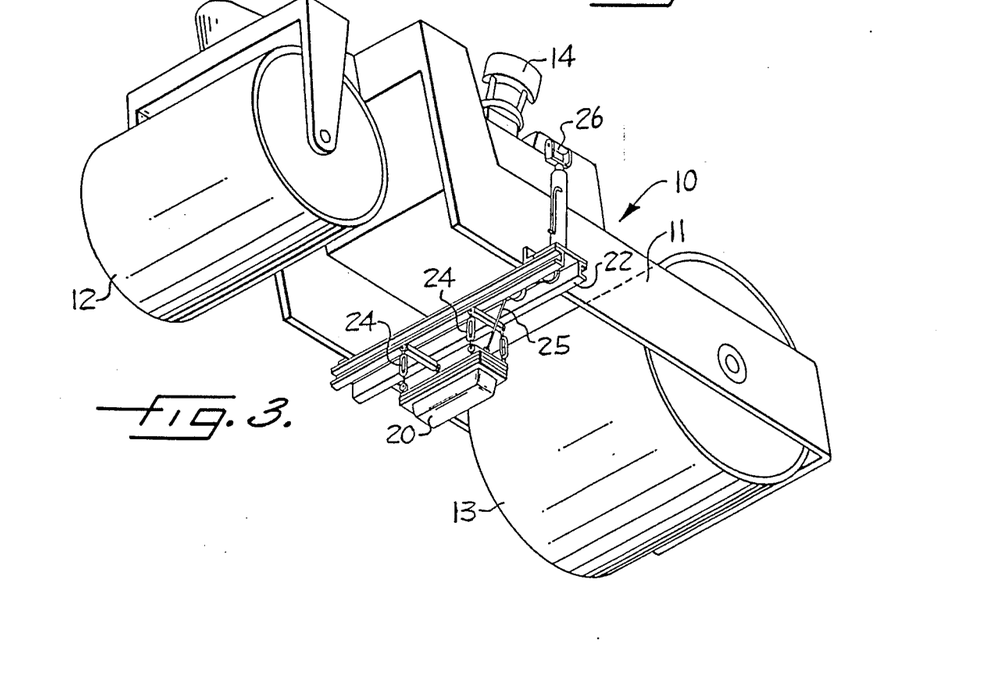
FIG. 3 is a perspective view thereof from the underside.
Figure 4:
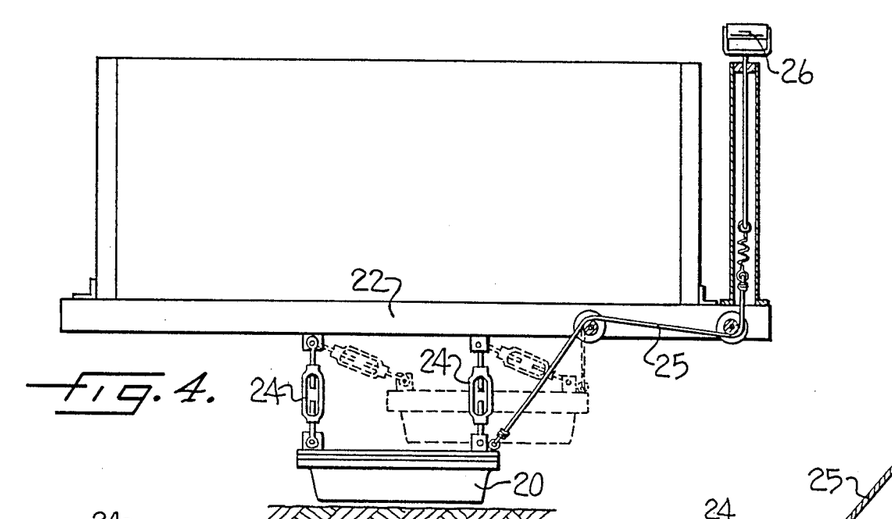
FIG. 4 is a vertical sectional view through the compactor vehicle taken substantially along the line 4—4 of FIG. 1 and showing the arrangements for mounting the sensor unit in suspended relation a short distance above the pavement surface and for retracting the detector unit during non-use.

As best seen in FIG. 1, means is provided on the underside of the compactor vehicle for mounting the sensor unit 20 in suspended relation a short distance, above the pavement surface. In the particular embodiment illustrated, the mounting means includes an elongate beam 22 mounted to the chassis 11 of the compactor vehicle and extending transversely thereacross. The sensor unit is suspended from the beam 22 by three adjustable mounting brackets 24. Brackets 24 are pivotally mounted to the beam, and in turn to the sensor unit 20 to provide freedom of movement to the sensor unit in all directions. Thus in the event that the sensor unit strikes an obstruction protruding above the pavement surface, it can freely swing out of the way and then return to its normal suspended operative position. As seen in FIG. 4, the mounting brackets 24 are constructed in the form of turnbuckles, to permit adjusting the height of the measurement unit and the spacing between the undersurface of the measurement unit 20 and the pavement surface. Nominally, this distance is about ½ inch.

As is also best seen in FIGS. 1 and 4, means is provided for raising the sensor unit 20 from its lowered operative position to a retracted non-use position where the sensor unit is safe from accidental contact with obstructions and the like. In the embodiment illustrated this takes the form of a cable 25 connected to measurement unit and an actuator handle 26 associated with the cable 25 and which is positioned at a location accessible to the operator. Prior to further discussion of the structure and operation of the gauge, it will be helpful to review some of the underlying principles of nuclear density gauge operation, particularly as applied to soil density measurement through an air gap.

The simplest method of measuring density involves the so-called backscatter method. To make this measurement, the source and detectors are both on the surface of the soil and gamma photons passing into the soil are scattered back to the detectors. If the soil had a density of zero, there would be nothing to cause scattering and the number of photons backscattered to the detector would be essentially zero. As the density of the soil increases, the number of backscattered photons increase with increase in density to a point where the backscattered photons are approximately equal to the losses due to additional scattering and absorption. The quantity of backscattered photons detected then becomes an approximate negative exponential function as the count decreases with increasing density of the soil.

The backscatter method, while simple to perform, is subject to error from various factors including surface roughness, soil composition, etc. Soil composition errors can be particularly significant. In an effort to improve accuracy and reduce soil composition error, the so-called "air gap density" method was developed. In this method a measurement is made with the gauge raised above the soil a predetermined height to form an air gap and a reading is obtained based upon both the thickness of the air gap and the composition of the soil. The air gap measurement can be used in combination with a flush, backscatter measurement to partially cancel out the composition error. Prior measurement methods have not been able to obtain a sufficiently accurate direct measurement of soil density through an air gap. Among other reasons, this is due to the fact that the counts are very sensitive to the size of the air gap. As the size of the gap increases, the count rate increases rapidly, since the soil density becomes a much less significant part of the average density seen by the detector.

In accordance with the present invention the density measurement is taken through an air gap, and means is provided for accurately measuring the air gap during the count and for adjusting the count rate in accordance with the measured air gap distance to obtain an accurate indication of soil density. The measurement of the air gap distance can be accomplished in various ways in accordance with the broad aspects of the present invention, including the use of ultrasonic means, laser means and capacitance, as well as nuclear methods. The preferred means and method as employed in the embodiment illustrated herein employs ultrasonic methods.

Figure 5:
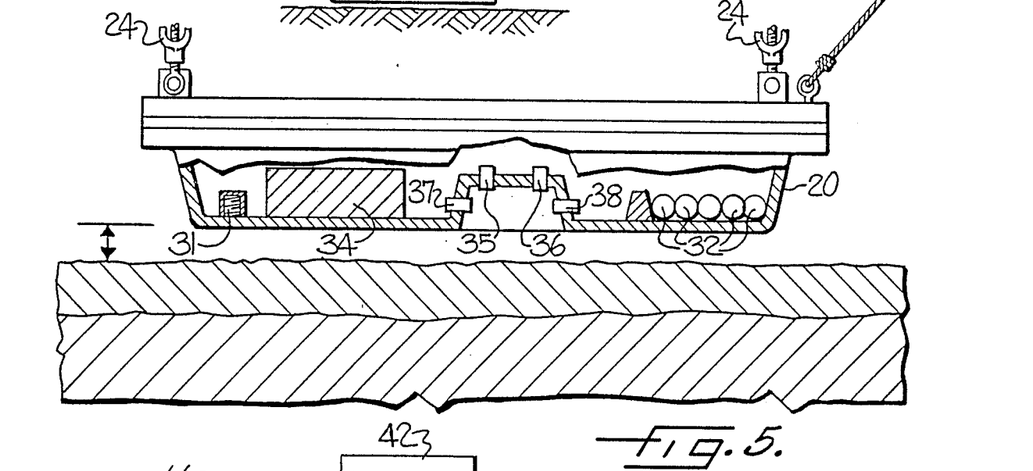
FIG. 5 is an enlarged view of the sensor unit of FIG. 4, with portions of the housing thereof broken away to show the interior components.

As best seen in FIG. 5, the measurement unit 20 comprises a housing 30 having a relatively smooth planar undersurface which is oriented generally parallel and in spaced relation to the pavement surface. The housing 30 encloses a suitable radiation source 31 and a detector means 32. The radiation source may be a CS-137 source of gamma radiation and the detector means may take the form of Geiger-Mueller tubes sensitive to photons. As illustrated, the source 31 is located adjacent to one end of the housing and the detector means 32 is mounted adjacent to the opposite end of the housing. Shielding 34 is provided around the source and around the detector means 32, as is conventional, to prevent radiation from reaching the detector means in a direct path from the source. Additionally, means (not shown) is provided for shielding the radiation source when the gauge is not being used for measurement.

As noted earlier, in an air gap measurement technique, the amount of radiation reaching a detector is a function of both the size of the air gap and the density of the material. The attenuation relationship for a given air gap for a single detector means, (e.g. for the detector means 32 illustrated) may be expressed as follows:

$$CR = Ae^{-BD} - C \qquad (I)$$

where:
CR is the count ratio, the detector count normalized by a standard reference count;
D is the density; and
A,B,C are the exponential curve fit parameters for the density vs. count ratio relationship for the given air gap.

The parameters A, B, and C are dependent on the size of the air gap between the gauge and the test material. If density measurements are taken on calibration standards of known density at a number of given air gap distances, one can derive a series of curves for the count ratio vs. density relationship at each air gap distance. Using suitable curve-fitting techniques, one can derive relationships for the density equation constants A, B, and C as a function of air gap such as the following:

$$A = a_1 + a_2G + a_3G^2 + a_4G^3 \quad \text{(II)}$$
$$B = b_1 + b_2G + b_3G^2 + b_4G^3$$
$$C = c_1 + c_2G + c_3G^2 + c_4G^3$$

where

A, B, C = constants from density equation I;

$a_1, a_2, a_3, a_4$ = constants determined empirically by gauge calibration;

$b_1, b_2, b_3, b_4$ = constants determined empirically by gauge calibration;

$c_1, c_2, c_3, c_4$ = constants determined empirically by gauge calibration; and G = Air gap distance between the gauge and the test material.

Knowing the air gap distance, one can calculate A, B, C for that air gap distance using equations (II) above and the empirically derived constants $a_1, a_2, a_3, a_4, b_1, b_2, b_3, b_4, c_1, c_2, c_3,$ and $c_4$. Then density D can be calculated from the density equation (I) above, or from the alternative form of the equation:

$$D = \frac{1}{B} \ln\left(\frac{A}{CR + C}\right) \quad \text{(III)}$$

In the illustrated embodiment of the invention ultrasonic means is utilized for measuring the air gap G between the test material and the measurement unit 20. As shown in FIG. 5, the ultrasonic means includes an ultrasonic transmitter 35 and a cooperating ultrasonic receiver 36 which are mounted in a recessed area or well on the underside of the housing 30 and aimed downwardly for measuring the distance to the underlying pavement surface. Additionally, the ultrasonic means also includes a reference transmitter 37 and cooperating receiver 38 mounted in the recessed well a predetermined distance apart and oriented generally horizontally toward one another for measuring the speed of sound in the air above the heated pavement or other underlying surface and producing a reference signal. This reference signal is utilized by the associated circuitry 54 to compensate for variations in the speed of sound due to changes in air temperature in the measuring region. These components and the associated electronic circuitry which is used in association therewith, as indicated at 54, are commercially available and their selection and use are within the capabilities of persons skilled in this art.

It should be understood that the foregoing description is intended as an illustration of one of a number of possible ways in which a density measurement can be obtained from the detector count data, and persons skilled in the appropriate arts will recognize that other particular solutions are possible within the broad scope and spirit of the present invention. For example, in commonly owned U.S. Pat. Nos. 4,525,854 and 4,641,030 techniques are disclosed whereby it is possible to obtain density readings which are weighed toward predetermined strata within a test material, and these principles may be utilized for obtaining density measurements in the present invention.

Figure 6:
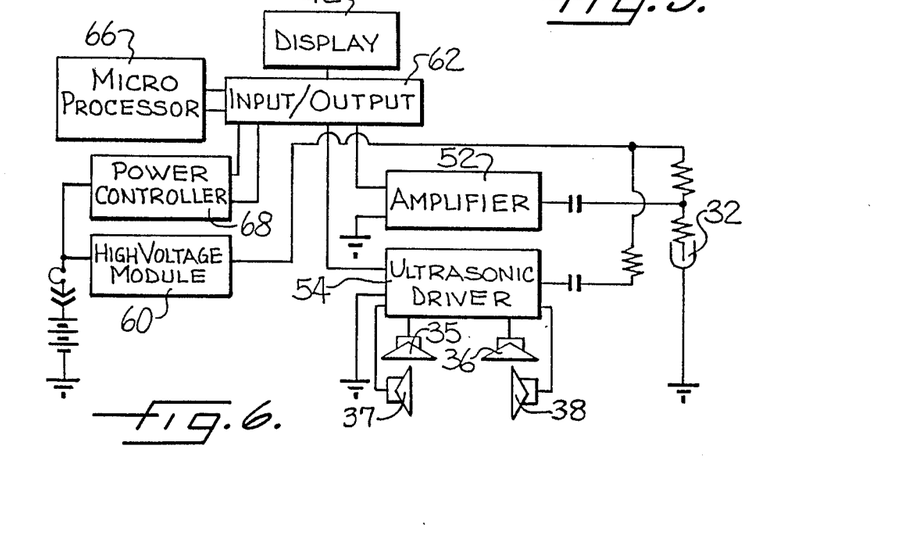
FIG. 6 is a schematic diagram of the electronic components of the instrument.
Figure 7:
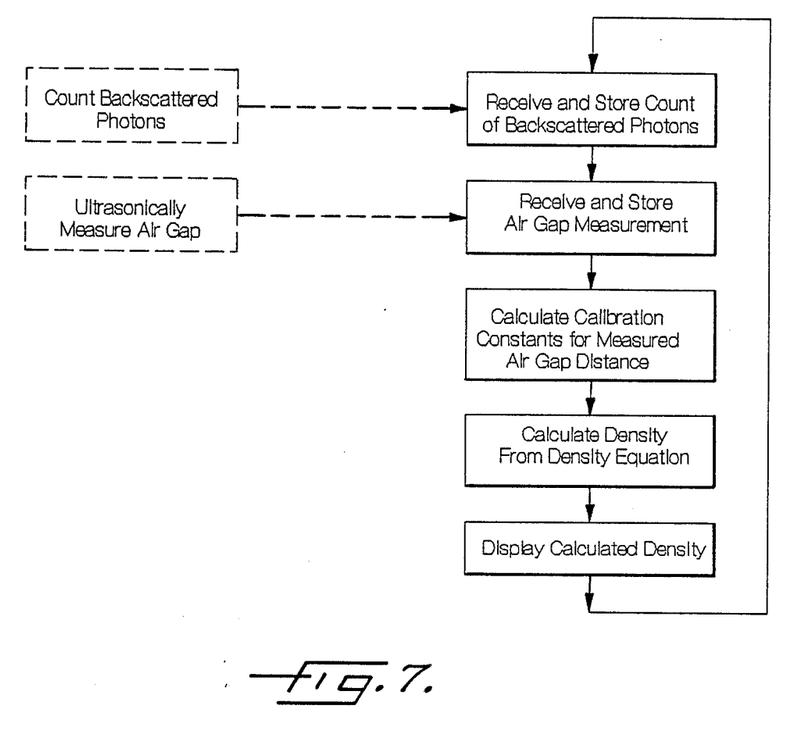
FIG. 7 is a flowchart illustrating how the density is calculated as a function of count of backscattered photons and air gap measurement.

Referring now to FIG. 6, the detector 32 is electrically connected with a corresponding amplifier 52. Additionally, as is required, the detector is connected with a source 60 of high voltage. Output from the amplifier 52 is directed to an input/output circuit generally indicated at 62 and is available through such circuitry to an electronic computing device, shown in the form of a microprocessor means 66, and to display 42. The microprocessor means 66 includes a commercially available microprocessor chip, together with associated memory means, such as an EPROM or EEPROM for storing program instructions and data constants, as well as random access memory (RAM) for storing other information, intermediate data and the like. The ultrasonic transmitter 35 and receiver 36 are connected to an ultrasonic driver which provides as an output a signal representative of the air gap distance. This signal is provided to the microprocessor through the input/output circuit 62. Power to the entire device is supplied by a power controller 68.

The microprocessor means 66 performs in the circuit of the present invention (as schematically illustrated in FIG. 6) a number of functions including governing time intervals for gauging in both "standard" and "measure" modes. The microprocessor means 66 also serves the function of a counter and recorder operatively associated with the detector for separately counting and recording the measured radiation information from the detectors and the distance signal from the ultrasonic device. In this regard, the radiation information preferably takes the form of a total radiation count for each Geiger-Mueller detector per time interval. In other embodiments the radiation information may take other forms, such as radiation count rates.

The microprocessor means 66 also serves to store the empirically derived constants $a_1, a_2, a_3, a_4, b_1, b_2, b_3, b_4, c_1, c_2, c_3,$ and $c_4$ which are needed for calculating the density equation constants A, B and C for a given air gap distance. In addition the microprocessor means stores, in appropriate form, the instructions needed for taking the radiation counts from detector means 32 and for calculating therefrom, using the density equation (III) above, the correct density value and for displaying the density values to the operator. These operations are indicated in flowchart form in FIG. 8. From this flowchart, persons of ordinary skill in the programming of microprocessors can readily produce the specific detailed instructions required to perform these operations in a particular microprocessor. Other functions, generally known to persons appropriately skilled in the art, are also performed by the microprocessor.

It is significant that the microprocessor means 66 operates in "real-time", so that the operator of the compactor vehicle rapidly receives a display of the density or degree of compaction which has been achieved. The "real-time" operation also provides a substantially instantaneous determination of the air gap distance, so that the correct density equation constants can be used in calculating density. When compacting hot bituminous paving mixes for example, the paving mix is somewhat resilient and spongy during the early stages of compaction, such that the rigid rollers of the compactor vehicle sink into the pavement to some degree. Later, as the paving material cools and hardens, the rollers of the vehicle do not sink as much. Thus the air gap between the measurement unit and the pavement surface varies during the compaction operation. A "real-time" instantaneous air gap measurement ensures that the density calculation remains accurate throughout the compaction operation.

In the drawings and specification, there has been set forth a preferred embodiment of the invention, and although specific terms are employed, they are used in That which is claimed is:

1. A method of measuring the density of a test material using a nuclear radiation backscatter gauge including nuclear radiation source and nuclear radiation detector means positioned in spaced relation to the source, said method comprising
    moving the source and detector means relative to the test material while maintaining the source and detector means in spaced relation above the surface of the test material to form an air gap therebetween,
    obtaining a count of the photons which are backscattered to the detector means by the test material,
    obtaining a measurement which represents the size of the air gap between the surface of the test material and the detector means by ultrasonically measuring the air gap while compensating for variations in the speed of sound due to changes in air temperature in the measuring region, and
    calculating the density of the test material as a function of said count of backscattered photons and said measurement of the air gap.

2. A method of measuring the density of a test material using a nuclear radiation backscatter gauge including nuclear radiation source and nuclear radiation detector means positioned in spaced relation to the source, said method comprising
    moving the source and detector means relative to the test material while maintaining the source and detector means in spaced relation above the surface of the test material to form an air gap therebetween,
    obtaining a count of the photons which are backscattered to the detector means by the test material,
    obtaining a measurement which represents the size of the air gap between the surface of the test material and the detector means, and
    calculating the density of the test material as a function of said count of backscattered photons and said measurement of the air gap wherein said step of calculating the density of the test material as a function of said count of backscattered photons and said measurement of the air gap comprises
    (a) calculating calibration constants A, B and C for the density equation $$D = \frac{1}{B} \ln\left(\frac{A}{CR + C}\right),$$

where CR is the count ratio and D is the density, as a function of the air gap measurement using an empirically derived relationship between the air gap measurement and such constants; and
    (b) applying the thus calculated calibration constants A, B and C in the density equation $$D = \frac{1}{B} \ln\left(\frac{A}{CR + C}\right)$$

to thereby determine the density of the test material.

3. A method of measuring the density of a test material using a nuclear radiation backscatter gauge including nuclear radiation source and nuclear radiation detector means positioned in spaced relation to the source, and computer means for performing real-time calculations, said method comprising
    moving the source and detector means relative to the test material while maintaining the source and detector means in spaced relation above the surface of the test material to form an air gap therebetween,
    obtaining a count of the photons which are backscattered to the detector means by the test material and storing said count as a value in said computer means,
    obtaining a measurement which represents the size of the air gap between the surface of the test material and the detector means and storing said air gap measurement as a value in said computer means, and
    storing in said computer means, values defining an empirically derived relationship between the air gap measurement and the calibration constants A, B and C for the density equation $$D = \frac{1}{B} \ln\left(\frac{A}{CR + C}\right),$$

where CR is the count ratio and D is the density,
    calculating with said computer means, values for the calibration constants A, B and C for said density equation using the stored values defining said empirically derived relationship and using said stored values for the air gap measurement; and
    calculating with said computer means, the density of the test material, using the thus calculated calibration constants A, B and C and the stored photon count in the density equation $$D = \frac{1}{B} \ln\left(\frac{A}{CR + C}\right)$$

4. A method of compacting materials with a compactor vehicle having compaction rollers which serve as wheels for the compactor vehicle, said method comprising
    driving a pavement compactor vehicle successively over the material to compact the material, while maintaining a nuclear radiation backscatter gauge in a spaced relationship above the surface of the material to form an air gap therebetween, and while directing photons from a nuclear radiation source in the gauge through the air gap and into the underlying material; obtaining a count of the photons which are backscattered from the material and received by a detector provided in the nuclear backscatter gauge;
    obtaining a measurement which represents the size of the air gap between the surface of the test material and the detector;
    calculating the density of the material as a function of said count of backscattered photons and said measurement of the air gap; and
    displaying to the operator of the compactor vehicle an indication of the thus calculated material density while the operator is driving the vehicle to thereby enable the operator to ascertain when a desired degree of compaction of the material has been attained.

5. The method according to claim 4 including the step of receiving input of a setpoint representing the desired target density to be attained in the material by operation of the compactor vehicle and comparing the measured density of the material with said setpoint while the compactor vehicle is being driven over the material and displaying to the operator when the desired target density has been attained.

6. The method according to claim 5 wherein said displaying step comprises displaying to the operator of the vehicle a first signal indicating that the density of material is below said setpoint and that further compaction of the material is required, and displaying to the operator of the vehicle a second signal when the desired setpoint has been attained.

7. A nuclear radiation backscatter gauge for measuring the density of a test material comprising a nuclear radiation source, nuclear radiation detector means mounted in predetermined spaced relation from said source, a sensor unit including a housing enclosing said source and said detector means, means for suspendingly mounting said housing in spaced relation from the surface of the material so that the source is positioned for emitting nuclear radiation through an air gap beneath the sensor unit and into the material and the detector means is positioned for detecting backscattered radiation for the material, means cooperating with said detector means for obtaining a count of the photons which are backscattered to the detector means by the test material, means for measuring the size of the air gap between the surface of the test material and the detector means, said means for measuring the size of the air gap comprising means for ultrasonically measuring the air gap and means for comprising for variations in the speed of sound due to changes in air temperature in the measuring region, and means for calculating the density of the test material as a function of said count of backscattered photons and said measurement of the air gap.

8. A nuclear radiation backscatter gauge for measuring the density of a test material comprising a nuclear radiation source, nuclear radiation detector means mounted in predetermined spaced relation from said source, a sensor unit including a housing enclosing said source and said detector means, means for suspendingly mounting said housing in spaced relation from the surface of the material so that the source is positioned for emitting nuclear radiation through an air gap beneath the sensor unit and into the material and the detector means is positioned for detecting backscattered radiation from the material, means cooperating with said detector means for obtaining a count of the photons which are backscattered to the detector means by the test material, means for measuring the size of the air gap between the surface of the test material and the detector means, and means for calculating the density of the test material as a function of said count of backscattered photons and said measurement of the air gap, wherein said means for calculating the density of the test material as a function of said count of backscattered photons and said measurement of the air gap comprises computer means including a stored set of instructions for (a) calculating calibration constants A, B and C for the density equation $$D = \frac{1}{B} \ln\left(\frac{A}{CR + C}\right),$$

where CR is the count ratio and D is the density, as a function of the air gap measurement using an empirically derived relationship between the air gap measurement and such constants; and (b) applying the thus calculated calibration constants A, B and C in the density equation $$D = \frac{1}{B} \ln\left(\frac{A}{CR + C}\right)$$

to thereby determine the density of the test material.

9. A compactor vehicle having rollers for compaction of materials, said rollers also serving as wheels for the compactor vehicle, a chassis connected to the rollers for receiving thereon the operator of the compactor vehicle, and motor means for propelling the compactor vehicle along the surface of the material; and in combination therewith nuclear density gauge means for measuring the density of the material during operation of the compactor vehicle, said gauge means comprising a nuclear radiation source, nuclear radiation detector means mounted in predetermined spaced relation from said source, a sensor unit including a housing enclosing said source and said detector means, means for suspendingly mounting said housing from said vehicle chassis in spaced relation from the surface of the material so that the source is positioned for emitting nuclear radiation through an air gap beneath the gauge means and into the material and the detector means is positioned for detecting backscattered radiation from the material, means cooperating with said detector means for obtaining a count of the photons which are backscattered to the detector means by the test material, means for ultrasonically measuring the size of the air gap between the surface of the test material and the detector means while compensating for variations in the speed of sound due to changes in air temperature in the measuring region, and means for calculating the density of the test material as a function of said count of backscattered photons and said measurement of the air gap.

10. A compactor vehicle having rollers for compaction of materials, said rollers also serving as wheels for the compactor vehicle, a chassis connected to the rollers for receiving thereon an operator of the compactor vehicle, and motor means for propelling the compactor vehicle along the surface of the material; and in combination therewith nuclear density gauge means for measuring the density of the material during operation of the compactor vehicle, said gauge means comprising a control unit mounted on the vehicle chassis at a location accessible to the compactor vehicle operator, a sensor unit operatively connected to said control unit and including a nuclear radiation source and nuclear radiation detector means mounted in predetermined spaced relation from said source, means for suspendingly mounting said sensor unit from the underside of said vehicle chassis with said source and detector means being located in spaced relation from the surface of the material so that the source is positioned for emitting nuclear radiation through an air gap beneath the gauge means and into the underlying material and the detector means is positioned for detecting backscattered radiation from the material, means cooperating with said detector means for obtaining a count of the photons which are backscattered to the detector means by the test material, means for measuring the size of the air gap between the surface of the test material and the detector means, means for calculating the density of the test material as a function of said count of backscattered photons and said measurement of the air gap, and means associated with said control unit for displaying to the operator of the compactor vehicle an indication of the thus calculated material density while the operator is driving the vehicle to thereby enable the operator to ascertain when a desired degree of compaction of the material has been attained.

* * * * *

UNITED STATES PATENT AND TRADEMARK OFFICE
CERTIFICATE OF CORRECTION

PATENT NO. : 4,979,197

DATED : December 18, 1990

INVENTOR(S) : William F. Troxler, Sr., et al.

It is certified that error appears in the above-identified patent and that said Letters Patent is hereby corrected as shown below:

Column 3, line 27, "c" should be -- C --.

Column 5, line 32, "Nominally" should be -- Normally --.

Column 11, line 29, "for" should be -- from --.

Column 11, line 37 "comprising" should be -- compensating --.

Signed and Sealed this

Thirtieth Day of March, 1993

Attest:

STEPHEN G. KUNIN

*Attesting Officer*     Acting Commissioner of Patents and Trademarks